United States Patent [19]

Eisenbraun

[11] Patent Number: 4,691,057

[45] Date of Patent: Sep. 1, 1987

[54] PROCESS FOR MAKING ALKALI METAL ARYLOXIDES

[75] Inventor: Allan A. Eisenbraun, Baton Rouge, La.

[73] Assignee: Ethyl Corporation, Richmond, Va.

[21] Appl. No.: 652,099

[22] Filed: Sep. 19, 1984

[51] Int. Cl.$^4$ .................. C07C 103/38; C07F 9/00
[52] U.S. Cl. ........................... 564/223; 564/443; 558/80; 568/630; 568/716; 568/774; 568/775; 568/780
[58] Field of Search ............ 260/927 R, 973; 568/716, 630, 774, 775, 780; 564/223, 443

[56] References Cited

U.S. PATENT DOCUMENTS

| | | | |
|---|---|---|---|
| 2,866,816 | 12/1958 | Heywood | 568/774 |
| 3,856,713 | 12/1974 | Rose et al. | 528/399 |
| 3,939,228 | 2/1976 | Kao | 260/973 |
| 4,593,129 | 6/1986 | Wilson, Jr. et al. | 568/716 |

*Primary Examiner*—Anton H. Sutto
*Attorney, Agent, or Firm*—Donald L. Johnson; John F. Sieberth; J. D. Odenweller

[57] ABSTRACT

The reaction of alkali metal with aromatic hydroxy compounds is promoted by inclusion of an alcohol in the reaction mixture. The alkali metal aryloxide formed can be reacted with phosphonitrilic chloride polymers to make polyaryloxyphosphazenes.

11 Claims, No Drawings

PROCESS FOR MAKING ALKALI METAL ARYLOXIDES

BACKGROUND OF THE INVENTION

Alkali metal aryloxides can be made by a number of procedures. For example, sodium reacts with phenol to yield sodium phenoxide. This reaction is usually conducted in an ether solvent for the phenoxide such as tetrahydrofuran to prevent the formation of a phenoxide coating on the sodium metal which inhibits the reaction. Alternatively, aryloxides can be made by reacting an aryl hydroxide with a reactive alkali metal compound such as sodium hydride or sodamide. Although these prior methods are effective, the reaction is usually slow and often incomplete. Therefore, a need exists for a process for making alkali metal aryloxides that is fast and goes to completion.

SUMMARY

It has been discovered that alkali metal aryloxides can be made in reduced time by the reaction of an alkali metal with an aryl hydroxide containing a promoter amount of an alcohol. The reaction proceeds to completion in an ether solvent giving an alkali metal aryloxide solution and/or suspension that can be used to introduce aryloxy substituents into phosphonitrilic chloride polymers.

DESCRIPTION OF THE PREFERRED EMBODIMENTS

A preferred embodiment of the invention is a process for making an alkali metal aryloxide comprising reacting an alkali metal with an aryl hydroxide compound in the presence of a promoter amount of a lower alcohol.

Alkali metals that can be used in the process include sodium and potassium. Because of economics and availability sodium is the preferred alkali metal.

The alkali metal may be used in the form of large chunks or small pieces. Preferably the alkali metal is reduced to very small pieces or more preferably is melted and dispersed in an inert liquid such as mineral oil or ethers. Dispersed particles can range from 0.5 up to 200 or more microns. The dispersion can be initially made in an inert non-solvent liquid such as mineral oil and the mineral oil then added to an ether solvent in which the reaction is conducted.

The reaction is applicable to a wide range of aryl hydroxide compounds which are capable of reacting with alkali metals to form alkali metal aryloxides. The aryl hydroxides may be mono or polynuclear, that is, they can contain one or more than one benzene ring. Representative aryl hydroxide compounds are phenol, o-cresol, m-cresol, p-cresol, p-ethylphenol, p-isopropylphenol, o-tert-butylphenol, α-naphthol, β-napthol, p-secoctylphenol, p-sec-eicosylphenol, o-allylphenol, p-allylphenol, p-(but-1-enyl)phenol, p-phenylphenol, p-(α-methylbenzyl) phenol, p-(α,α-di-methylbenzyl)-phenol, o-cyclohexylphenol, p-cyclohexylphenol, p-methoxyphenol, o-butoxyphenol, p-butoxyphenol, p-hexyloxyphenol, p-dodecyloxyphenol, p-phenoxyphenol, m-phenoxy phenol, p-acetylphenol, p-butyrylphenol, m-acetoxyphenol, p-acetoxyphenol, p-butyryloxyphenol, p-acetamidophenol, o-acetamidophenol, p-butylamidophenol, p-diacetylimidophenol, p-methylaminophenol, p-dimethylaminophenol, o-ethylaminophenol, p-n-butylaminophenol, o-dioctylaminophenol, p-chlorophenol, 2,4-di-chlorophenol, p-bromophenol, p-fluorophenol, 2,4-di-fluorophenol, p-trifluoromethylphenol, p-(2-chloroethyl)phenol, p-nitrophenol, p-tert-butylphenol, p-propionylphenol, p-propionylamidophenol and the like.

The preferred aryl hydroxides are phenol and substituted phenols wherein the phenol substituents are selected from alkyl (e.g. methyl, ethyl, n-propyl, isopropyl, n-butyl, tert-butyl, sec-octyl, sec-eicosyl, etc.), alkenyl (e.g. allyl, but-2-enyl, oct-3-enyl, etc.), alkoxy (e.g. methoxy, ethoxy, n-propoxy, isopropoxy, butoxy, isobutoxy, sec-butoxy, etc.), aryloxy (e.g. phenoxy, o-cresoxy, p-cresoxy, p-isobutylphenoxy, etc.), acyl (e.g. acetyl, butyryl, octanyl, octadecanyl, etc.), acyloxy (e.g. acetoxy, propionoxy, butyryloxy, dodecanyloxy, etc.), acylimido (e.g. diacetylimido, dipropionylimido, dibutyrylimido, etc.), acylamido (e.g. acetamido, propionamido, decanoylamido, octadecanolyamido, etc.), alkyl amino (e.g. methylamino, ethylamino, n-propylamino, isobutylamino, n-butylamino, etc.), dialkylamino (e.g. dimethylamino, diethylamino, methylethylamino, methyloctylamino, etc.), halogens (e.g. chloro, bromo, fluro, iodo) and haloalkyls (e.g. trifluromethyl, trichloromethyl, fluorodichloromethyl, 2-chloroethyl, 2,2-dichloroethyl, 2,2,2-trifluoroethyl, 4-bromobutyl, etc.) and nitro, e.g. p-nitrophenol.

The most preferred phenol substituent groups are alkyl, alkenyl, alkoxy and acylamido.

The amount of alkali metal should be about equivalent to the aryl hydroxide. A useful range is about 0.9–1.2 equivalents of alkali metal per equivalent of hydroxyl group.

The preferred alcohols are those that are reactive with alkali metals while exhibiting lower acidity than the aryl hydroxide compound used in the process. Illustrative examples include methanol, ethanol, isobutanol, tert-amyl alcohol, 2-ethyl hexanol and the like. The preferred alcohols are the lower alcohols such as methanol, ethanol and isopropanol.

The amount of alcohol need only be a promoter amount. The amount needed to promote the reaction is readily determined experimentally. A useful range of alcohol is about 0.01–5.0 moles of alcohol per mole of aryl hydroxide. A more preferred range is 0.05–0.5.

The reaction is preferably conducted in an inert ether solvent such as tetrahydrofuran, dimethoxyethane, diethoxyethane, dimethylether of diethyleneglycol, diethyl ether of diethyleneglycol, dibutyl ether of diethyleneglycol, dioxane, mixtures of the ethers and the like. The amount of ether should be sufficient to partially or fully dissolve the alkali metal aryloxide under the reaction conditions. A useful range is about 50–1000 parts by weight ether per each 100 parts by weight aryl hydroxide. In certain cases, such as in an industrial process, one may prefer to conduct the reaction without solvents.

The reaction can be conducted at any temperature high enough to cause the reaction to proceed but not so high as to cause decomposition. In general, the reaction is preferably conducted at a temperature of about 20° C. up to reflux temperature. If desired, higher temperatures can be used if the reaction is conducted under pressure. Hydrogen is evolved during the reaction so adequate ventilation must be provided for safety purposes.

The alkali metal aryloxide made by the process can be used wherever an alkali metal aryloxide reactant is required. The alkali metal aryloxides are especially useful in a process for introducing aryloxide substituents into polyphosphazenes. This can be accomplished by reacting the alkali metal aryloxide with a phosphonitrilic chloride polymer. Accordingly, another preferred embodiment of the invention is a process for making an aryloxy-substituted polyphosphazene selected from cyclic and linear polyphosphazenes, said process comprising reacting an alkali metal with an aryl hydroxide which contains a promoter amount of a lower alcohol to obtain an alkali metal aryloxide and then reacting the alkali metal aryloxide with a cyclic or linear phosphonitrilic chloride polymer to obtain an aryloxy substituted polyphosphazene.

Phosphonitrilic chloride polymers are well known. The simplest of these are the cyclic polymers which contain about 3–7 [PNCl$_2$] groups forming a ring of alternating phosphorus and nitrogen atoms. The most common cyclic polymers are trimers and tetramers, especially trimer. The individual cyclic polymers can be separated by means such as distillation or crystallization or the crude mixture of cyclic phosphonitrilic chloride can be used when a pure aryloxy substituted polymer is not required.

The phosphonitrilic chloride polymers are made by reacting ammonium chloride and phosphorus pentachloride in a solvent such as monochlorobenzene at temperatures in the range of about 100° C. up to reflux. Reaction stoichiometry is about one mole of NH$_4$Cl per mole of PCl$_5$. Yield of cyclic phosphonitrilic chlorides is maximized by use of a stoichiometric excess of NH$_4$Cl over PCl$_5$. Use of excess PCl$_5$ favors formation of mainly linear oligomers containing about 3–15 or more [PNCl$_2$] units and terminated with various phosphorus groups such as =PCl$_2$, —PCl$_3{}^+$ PCl$_6{}^-$, —PCl$_3{}^+$ Cl$^-$ and the like.

High molecular weight linear phosphonitrilic chloride polymers can be made by the thermal polymerization of the cyclic polymers. Preferably, cyclic trimer is purified by various means including distillation, crystallization, water washing and the like. The highly purified trimer can then be heated to about 200°–250° C. in an inert atmosphere or under high vacuum to form high molecular weight linear polymer. Preferably a catalyst such as AlCl$_3$, BBr$_3$ or a BCl$_3$ triphenylphosphate complex is added to the polymerization mixture as described in U.S. Pat. No. 4,123,503 or U.S. Pat. No. 4,226,840. The resultant high molecular weight phosphonitrilic chloride polymer can be purified by dissolving the polymerization mixture in a solvent such as toluene or cyclohexane followed by precipitation of the high molecular weight linear phosphonitrilic chloride polymer by the addition of a non-solvent aliphatic hydrocarbon, e.g. hexane. The precipitated high molecular weight linear phosphonitrilic chloride polymers contain about 50–50,000 or more [PNCl$_2$] units. Hence, the linear phosphonitrilic chloride polymers including both low and high molecular weight polymers contain, as a group, 3 to about 50,000 or more [PNCl$_2$] units.

The preferred phosphonitrilic chloride polymers are the cyclic phosphonitrilic chlorides especially trimer or mixtures containing trimers.

The aryloxide substitution reaction is conducted by dissolving the phosphonitrilic chloride polymer, whether linear or cyclic, in a solvent such as cyclohexane, toluene, xylene or an ether as previously described and adding the solution to an ether solution of the alkali metal aryloxide and reacting at about 110°–160° C. as described in U.S. Pat. No. 3,856,713. Generally, a slight stoichiometric excess of alkali metal aryloxide over covalent chloride groups is used. The reaction is continued until all or most of the covalent chlorine has reacted. Reaction is usually complete in about 0.5–8 hours.

The following example serves to illustrate how the process can be conducted:

EXAMPLE 1

Preparation of the Alkali Metal Aryloxide

In a reaction vessel was placed 100 ml dry tetrahydrofuran (THF) and 28.8 g. of a sodium-mineral oil dispersion (39.6 wt. % Na, 0.496 gram equivalents of Na). The mixture was stirred and a solution of 78.2 g. (0.517 moles) of 4-acetamidophenol in 250 ml dry THF was added slowly followed by a solution of 10 g. methanol in 70 ml dry THF. The reaction mixture was stirred at reflux until all the sodium had reacted to form a sodium 4-acetamidophenoxide which for the most part separated as a solid crystal phase.

Preparation of a Phenoxide-Substituted Polyphosphazene

To the above mixture was added a solution of 21.78 g. (0.0626 moles, 0.37 equivalents of chloride) of cyclic phosphonitrilic chloride trimer in 200 ml dry THF. The mixture was stirred at reflux for 16 hours after which $^{31}$P-NMR analysis showed that 91% of the trimer had formed hexakis-(4-acetamidophenoxy)cyclotriphosphazene. The reaction mixture was cooled to precipitate the product which was recrystallized twice from methanol. The purified product (mp 254°–5° C.) analyzed 55.81% C, 4.76% H, 11.65% N and 8.94% P (calculated 55.69% C, 4.67% H, 12.17% N and 8.97% P).

EXAMPLE 2

A solution of 43.74 g (0.2893 mole) of 4-acetamidophenol in 150 ml THF was stirred and heated under reflux. A mixture consisting of 16.0 g of sodium (0.2756 mole) dispersion (39.6 wt % Na) in mineral oil and 150 ml THF was added slowly. A vigorous reaction took place initially, which soon subsided. Ten ml methanol was then added which caused a vigorous reaction to occur. A solution of 14.52 g (0.04176 mole) of cyclic phosphonitrilic chloride trimer in 150 ml THF was then added over a period of 0.5 hours and the mixture was allowed to stir under reflux for an additional 16 hours. Analysis of the reaction mixture by P$^{31}$ NMR showed that 26% of the phosphorus was converted to the desired hexakis-(4-acetamidophenoxy)cyclotriphosphazene.

To the above mixture was added a solution of 8.2 g (0.0542 mole) of 4-acetamidophenol in 100 ml THF and, a mixture of 3.0 g of a 39.6% dispersion of metallic sodium in mineral oil (0.052 mole sodium) and 50 ml THF. The resulting mixture was stirred and heated under reflux for an additional 16 hours then neutralized with about 1.5 g acetic acid and allowed to cool. The mixture was then separated by filtration. The filtered product after drying weighed 65.17 g. $^{31}$P NMR analysis showed that all the phosphorus was present as the desired hexakis(4-acetamidophenoxy)cyclotriphosphazene.

EXAMPLE 3

Comparative Example

In a reaction vessel was placed 300 ml dry THF and 13.8 g. of a sodium-paraffin dispersion (50 wt % Na, 0.30 gram equivalents of Na). To this was added a solution of 46.3 g. (0.306 moles) of 4-acetamidophenol in 1250 ml dry THF. A voluminous precipitate formed which would not dissolve when stirred at reflux for 30 minutes. A solution of 17.38 g. (0.05 moles, 0.3 equivalents of chloride) in 70 ml dry THF was added and the mixture stirred at reflux for 16 hours. The reaction mixture was added to water forming a crystalline precipitate which analyzed $^{31}$P-NMR to show a number of different products but only 14.7 wt. % of the phosphorus was present as hexakis(4-acetamidophenoxy)cyclotriphosphazene compared to 91% in Example 1 and 100% in Example 2 following the present process.

I claim:

1. A process for making an alkali metal aryloxide, said process comprising reacting an alkali metal with an aromatic hydroxy compound in the presence of a promoter amount of a lower alcohol.

2. A process of claim 1 wherein said aromatic hydroxy compound is selected from the group consisting of phenol and substituted phenols.

3. A process of claim 2 wherein the phenol substituents are selected from the group consisting of alkyl, alkenyl, alkoxy, aryloxy, acyl, acyloxy, acylimido, acylamido, alkylamino, dialkylamino, halogen, haloalkyl and nitro.

4. A process of claim 1 wherein said alcohol is selected from the group consisting of methanol, ethanol, n-propanol, isopropanol, n-butanol, sec-butanol, isobutanol and tert-butanol.

5. A process of claim 4 wherein said aromatic hydroxy compound is selected from the group consisting of phenol and substituted phenol wherein said phenol substituents are selected from alkyl, alkenyl, alkoxy and acylamido and said alkali metal is sodium.

6. A process of claim 5 wherein said promoter amount is about 0.01-5.0 moles of alcohol per mole of said aromatic hydroxy compound.

7. A process of claim 1 conducted in an ether solvent.

8. A process of claim 7 wherein said ether solvent is selected from the group consisting of tetrahydrofuran, dimethoxyethane, diethoxyethane, dimethyl ether of diethylene glycol, diethyl ether of diethylene glycol, dioxane and mixtures thereof and said alkali metal is sodium.

9. A process of claim 8 wherein said alcohol is methanol.

10. A process of claim 9 wherein said aromatic hydroxy compound is selected from the group consisting of phenol and substituted phenols wherein said phenol substituents are selected from alkyl, alkenyl, alkoxy and acylamido.

11. A process of claim 10 wherein said aromatic hydroxy compound is acylamidophenol.

* * * * *